United States Patent [19]
Causton et al.

[11] Patent Number: 5,843,413
[45] Date of Patent: Dec. 1, 1998

[54] ANTIPERSPIRANTS AND METHOD OF APPLYING ANTIPERSPIRANT USING A SHAPED ARTICLE

[75] Inventors: Brian Edward Causton, Berkshire; Frederick Charles Baines, Bedfordshire, both of United Kingdom

[73] Assignee: The Gillette Company, Boston, Mass.

[21] Appl. No.: 640,771

[22] PCT Filed: Nov. 8, 1994

[86] PCT No.: PCT/GB94/02447

§ 371 Date: May 7, 1996

§ 102(e) Date: May 7, 1996

[87] PCT Pub. No.: WO95/13046

PCT Pub. Date: May 18, 1995

[30] Foreign Application Priority Data

Nov. 8, 1993 [GB] United Kingdom .................. 9322962

[51] Int. Cl.⁶ ............................ A61K 7/32; A61K 31/74; A61K 7/00
[52] U.S. Cl. .................... 424/65; 424/78.02; 424/78.08; 424/78.17; 424/400; 424/401
[58] Field of Search .............................. 424/65, 400, 401, 424/78.02, 78.08, 78.17

[56] References Cited

U.S. PATENT DOCUMENTS

| 3,317,394 | 5/1967 | Fryklof et al. ........................... 167/82 |
| 3,682,848 | 8/1972 | Virnelson . |
| 4,723,860 | 2/1988 | Giblin et al. ............................ 401/208 |

FOREIGN PATENT DOCUMENTS

| 0154465 | 2/1983 | European Pat. Off. . |
| 0164644 | 6/1985 | European Pat. Off. . |
| 0363137 | 4/1991 | European Pat. Off. . |
| 2302752 | 3/1971 | France . |
| 8909066 | 11/1992 | WIPO . |

*Primary Examiner*—Shelley A. Dodson
*Attorney, Agent, or Firm*—Stephan P. Williams

[57] ABSTRACT

A water-insoluble porous cross-linked polymeric matrix contains an antiperspirant in its pores, the pores being interconnected to permit the antiperspirant to be leached therefrom with water, with zero order release without change in pore geometry. The pores may additionally contain one or more other materials such as deodorants, moisturizers, lubricants and perfumes. The matrix can be shaped for application to the skin. An antiperspirant dispenser can comprise a matrix of the invention with a water reservoir therefor.

11 Claims, 5 Drawing Sheets

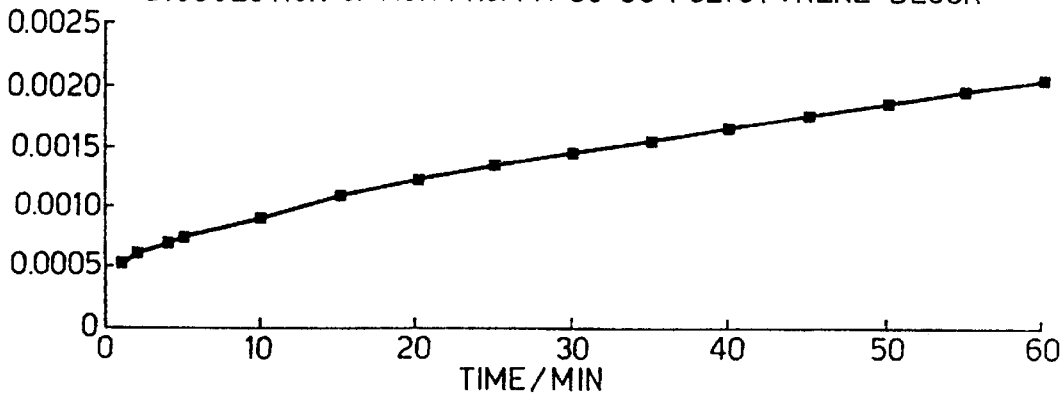
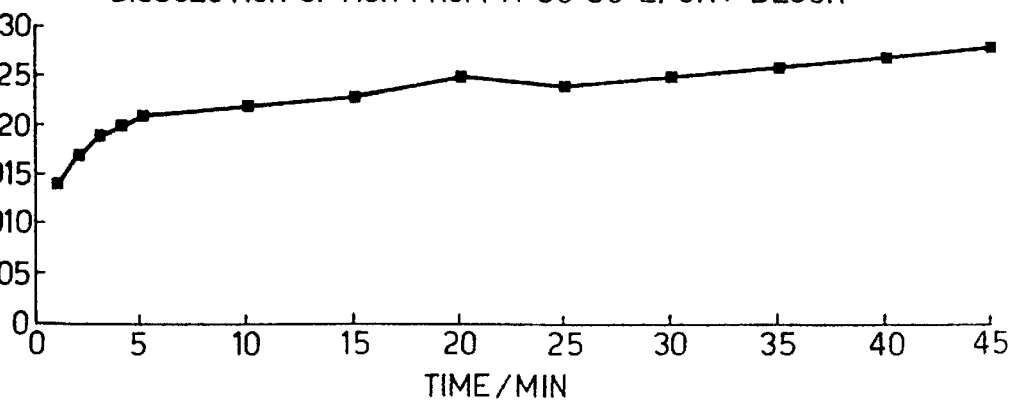

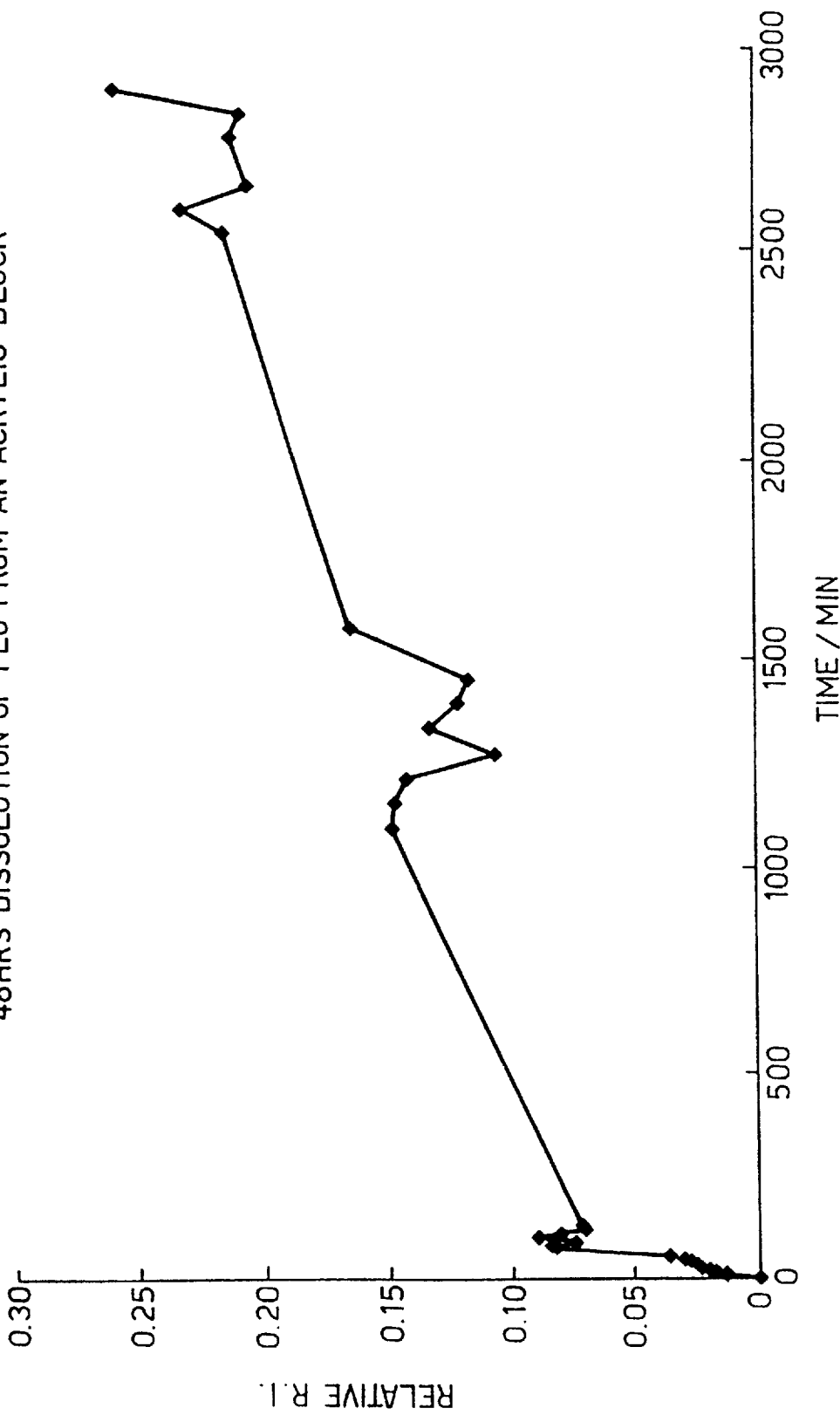

ANTIPERSPIRANTS AND METHOD OF APPLYING ANTIPERSPIRANT USING A SHAPED ARTICLE

This invention relates to antiperspirants and, more particularly, to a new antiperspirant product.

Antiperspirants are sold in three formulations, namely as aerosols (aluminium chlorhydroxide complex (ACH)), and in the zirconium form as roll-ons and wax-like sticks. Mixing the active antiperspirant with other substances in these formulations, particularly in roll-ons and sticks, can cause a significant reduction in the efficacy of the product in reducing the production of perspiration. Whilst aerosols do not suffer so much from this problem, there is currently a move away from aerosol type formulations for environmental reasons.

We have now devised a new antiperspirant product which is not an aerosol and which does not necessitate the use of materials which significantly reduce the efficacy of the antiperspirant material therein.

In accordance with a first aspect of the present invention, the antiperspirant product comprises a water-insoluble, porous, cross-linked polymeric matrix having an antiperspirant homogeneously distributed therein in interconnecting pores thereof, the product being in the form of a hard shape from which the antiperspirant can be released by water leaching with zero order release without change in the pore geometry.

The polymeric matrix is water-insoluble and serves to hold the antiperspirant therein until it is required. There are a lot of suitable materials from which the matrix may be made, for example polyurethanes, epoxy resins, polyolefins, polystyrene, polyvinyl chloride, phenol formaldehydes, silicones, poly(meth)acrylates, polyamides and poly(meth)acrylamides. We prefer to use cross-linked polymers made from ethylenically unsaturated monomers, for example cross-linked polyacrylates or polymethacrylates, such as poly(bisphenol A) propyl dimethacrylate, ethylene glycol dimethacrylate, triethylene glycol dimethacrylate or tetraethylene glycol dimethacrylate.

The product is made by mixing the matrix-forming materials with the antiperspirant, and then polymerising and/or cross-linking. According to a second aspect of the invention, there is provided a method of making a product of the invention, which method comprises forming a mixture of an antiperspirant and matrix-forming materials; and polymerising and/or cross-linking the matric-forming materials to form a water-insoluble, porous, cross-linked polymeric matrix with the antiperspirant homogeneously distributed therein in interconnecting pores thereof.

The antiperspirant is substantially homogeneously distributed throughout the matrix. The relative amounts of ACH and matrix-forming materials can vary widely. For example, on a weight basis, the product can comprise up to about 99% ACH, or up to about 95% matrix-forming material. More usually, the amount of ACH is from 30 to 80%, most preferably from 60 to 70%. The amount of polymeric matrix is usually from 20 to 60%, most preferably from about 20 to 35%.

The antiperspirant must be phase-separated from the matrix-forming materials so that it forms the pores in the final matrix. Normally, solid antiperspirant is used but liquid solutions can be employed. When an aqueous solution is used, it will dry out to leave a solid within, for example, 24 hours.

The precise nature of the active antiperspirant used in the products of this invention is not critical. Any material with antiperspirant properties can be used including, of course, those presently in common use in the art. Since it is not necessary in the present invention to use any significant amount of other materials, the efficacy of the antiperspirant as applied to the skin can be comparable with fresh "hot room" solutions, i.e. up to 80% sweat reduction or more can be achieved compared with the 50% or less associated with currently marketed forms of antiperspirant.

We have found that in use of the products of the invention, the active antiperspirant displays bactericidal properties.

The product can be made in any desired shape. A simple stick or other shape can be provided, for use with or without a holder. However, other shapes are equally possible. In one preferred arrangement, the shaped product is associated with a unit therefor, which unit includes a water reservoir for wetting the shape immediately prior to use.

The products of the invention can include other materials in addition to the antiperspirant as desired. Such additives include, for example, oral deodorants such as cetyl pyridinium chloride, and cosmetically efficacious materials such as moisturisers, eg. propylene glycol or glycerine; foaming agents, eg. fatty alcohol sulphates, alkyl benzene sulphonates, betaines or sulphosuccinates; antihistamines, eg. embramine or phenylloloxamine; anti-inflammatory compounds, eg. aloe vera or allantoin; lubricants such as polyethylene oxides, perfumes and fragrances, and substances such as menthol to give a soothing cooling sensation. These additives are water leachable from the product together with the antiperspirant. The products of the invention can contain large quantities of these materials, eg. up to 95% by weight, but normally they are present in minor amount, eg. up to 25%, and most usually in amounts of up to about 5% each.

When one or more of these additives is present in addition to the antiperspirant, the product of the invention is made as above described, i.e. by mixing the matrix-forming monomers with the antiperspirant and additive and then polymerising. The antiperspirant and any additive need to be in a discreet phase from the matrix-forming materials so as to form the pore structure in the final matrix and to be leachable therefrom. Sometimes it may be desired to incorporate an additive material which tends to dissolve in the matrix-forming materials and act, for example, as a plasticiser. According to a further aspect of the present invention, this problem can be overcome by lowering the temperature of the mixture to a level at which the additive becomes insoluble and forms a discreet dispersed phase. One example of such an additive is menthol which can dissolve in certain acrylic resins. By lowering the temperature, eg. to below 0° C. and lower, the menthol is insolubilised. The resin can then be cured at the low temperature, for example using blue light. Another example is polyethylene oxide. This technique of low temperature curing is, of course, also useful where heat-sensitive additives are involved.

In the products of the invention, the porous structure is essentially rigid so that, as the water-soluble antiperspirant (and any additive) is leached out, the pore geometry does not change. There is not usually any advantage in having a very hard brittle matrix, and indeed this can be disadvantageous. In order to give a softer feel, we prefer to have a water-insoluble plasticiser in the polymer. The choice of plasticiser will depend on the polymeric matrix, as will be clear to those skilled in the art, but for acrylic resins we prefer to use tetrahydrofuran (THF) methacrylate and/or $C_{12}$ methacrylate for this purpose. (By $C_{12}$ methacrylate, we mean methacrylate with a $C_{12}$ alkyl chain, the $C_{12}$ being an average chain length for the substituents.) The amount by weight of THF methacrylate is up to about 95%, preferably up to about 10%, most preferably around 5%. The amount by weight of $C_{12}$ methacrylate is up to about 90%, preferably up to about 15%, most preferably around 7%.

In the products of the invention, the antiperspirant (and any additive) is held within the matrix until it is to be used. Then the product is wet with water and applied to the user's skin. The water leaches the antiperspirant (and any additives) out of the matrix. The life of the product will depend on the degree to which it is used and on the original loading of antiperspirant in the matrix. However, regular daily use of a stick as an antiperspirant can provide at least two week's effective protection. The formulation should of course be stored dry between uses.

The antiperspirant (and any additive) is held in pores in the matrix structure. As is well known in the polymer art, the size and interconnecting of pores in such matrices can be closely controlled. For the purposes of the present invention, the pore properties should be such as to provide suitable water-leachability of the antiperspirant until the matrix is substantially exhausted. The pore size can vary widely, but will normally be in the range from 2 microns up to 2 mm. It is determined by the size of the ACH (and other actives), and this sizing can be controlled by ball milling, for example. A particle size of 10 to 25 microns, eg. about 15 microns, for the ACH is often used, but other sizes can be accommodated.

It is a feature of the invention that the release of antiperspirant (and any additive) is a zero order release, i.e. there is a substantially constant release rate independent of the amount of antiperspirant remaining in the product (until near to depletion). This is due to the fact that, as the antiperspirant is removed, the pore geometry is substantially unaffected.

In the course of use, the surface of the matrix may be or become roughened due to its porous nature. For user comfort, a lubricant such as a polyoxyethylene polymer may be included in the matrix. Alternatively, the surface of the product can be especially smoothed or polished in those areas designed to contact the user's skin.

In order to provide some signal of impending exhaustion of antiperspirant from the formulation, an indicator can be provided. For example, a water-soluble coloured material can be located at or near the centre of the matrix so that, as the last amounts of antiperspirant are leached out, the indicator begins to appear at the surface.

A particularly important feature of the present invention is that the new product of antiperspirant requires little or no packaging. The dry shape can be handled without any wrapping at all: alternatively a single plastics film covering is all that is necessary. The fact that the product can be provided in any desired shape provides wide possibilities for marketing.

In order that the invention may be more fully understood, reference will hereafter be made to the accompanying drawings, in which:

FIGS. 5 to 10 are dissolution curves of ACH and other materials from products of the invention made in Examples 3,4,5,7 and 8.

In order that the invention may be more fully understood, the following Examples are given by way of illustration only.

EXAMPLE 1

Aluminium chlorhydrol (2 g) was mixed with a solution (0.5 g) of Hitad (acrylic resin), camphorquinone and dibutyl tin dilaurate to form a smooth paste. (Hitad is an aromatic diacrylate diluted with a dimethylacrylate.) The paste was pressed under a force of 1 ton into a circular tablet which was cured on each side for 10 minutes with blue light (247 nm) at room temperature. The constitution of the tablet was:

|  | % |
| --- | --- |
| Hitad (London Resin Co. Ltd.) | 19.6 |
| Camphorquinone | 0.2 |
| Dibutyl tin dilaurate | 0.2 |
| Aluminium chlorhydrol | 80.0 |

Upon wetting with water, the aluminium chlorhydrol was leachable from the tablet. The tablet structure itself remained intact and the aluminium chlorhydrol was released until the supply was exhausted.

EXAMPLE 2

A homogeneous solution was made by mixing together at room temperature:

|  | Wt. parts |
| --- | --- |
| Hitad acrylic resin (London Resin Co. Ltd) | 90 |
| THF methacrylate | 5 |
| $C_{12}$ methacrylate | 10 |
| Camphorquinone | 1 |
| Dibutyl tin dilaurate | 1 |

Aluminium chlorhydrate (ACH) was also included in amounts varying from 5 to 50% by weight of the total mixture.

Figure 1:
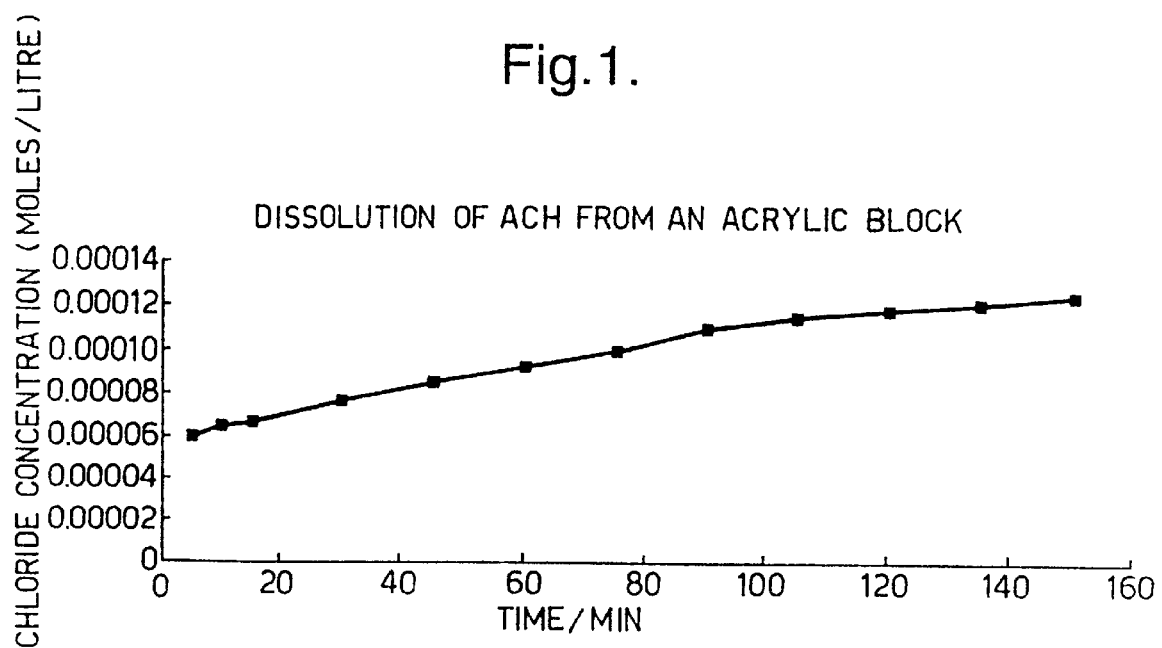
FIG. 1 is a graph of ACH release against time for a product of the invention as described in Example 2.

The mixtures were cured into flat blocks 12 mm×16 mm×2.5 mm using light of wavelength 247 mm. Cure times of 15 minutes were used. The cured blocks were then tested for the rate of release of the ACH. The blocks were each placed in a stainless steel infuser in 250 ml stirred water at 25° C. The ACH release was measured using a chloride electrode, and the results for the block containing 50% by weight ACH are shown in FIG. 1. It can be seen that release of ACH from the blocks was linear with time. The other blocks containing (initially) different amounts of ACH gave similar results.

A block made in the same way but containing 50% ACH and 5% polyethylene oxide (PEO) had improved lubricity over a block without the PEO. The PEO was of molecular weight 5,000,000.

EXAMPLE 3

ACH was mixed with the A and B parts of Rhone-Poulenc's Rhodorsil Silicone RTV-2 in the proportions given below. The mixture was poured into a mould 4×11×16 mm and allowed to cure at 20° C. for 24 hours. When placed in water at 28° C., the dissolution curve shown in FIG. 5 was obtained.

| Material A | 3.0 g |
| --- | --- |
| Material B | 0.3 g |
| ACH | 3.3 g |

Figure 5:
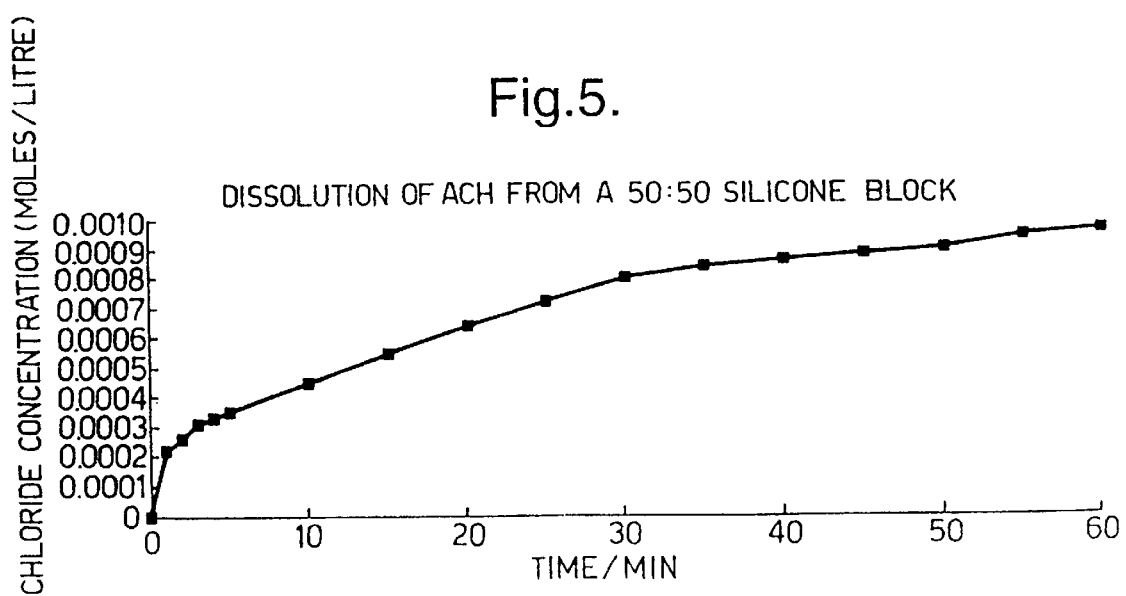

As can be seen from FIG. 5, the ACH which is distributed throughout the silicone matrix, leaches out with essentially zero order release.

EXAMPLE 4

A paste of ACH and styrene, to which had been added divinyl benzene (crosslinking agent), camphorquinone (light-activated initiator) and dibutyl tin dilaurate (initiator), was made as follows:

| | |
|---|---|
| Styrene | 2.0 g |
| Divinyl benzene | 0.3 g |
| Camphorquinone | 0.5 g |
| Dibutyl tin dilaurate | 0.5 g |
| ACH | 2.3 g |

The paste was packed into a mould 4×11×16 mm and cured by shining light of wavelength 247 nm on to the paste for 10 minutes.

The hard cured moulded shape was immersed in water and the concentration of ACH leaching therefrom into water at 28° C. was measured against time to provide the dissolution curve shown in FIG. 6. As can be seen, the ACH leaches out with essentially zero order release.

EXAMPLE 5

The following epoxy resin premix A was mixed 50:50 (by weight) with ACH and the mixture packed into a mould 4×11×16 mm and cured for 18 hrs. at 60° C.

| | |
|---|---|
| Epoxy premix A: | |
| Dodecyl succinic anhydride | 1.25 g |
| Diglycidyl ether of bisphenol A | 1.125 g |
| Benzyldimethylamine | 0.125 g |
| Mixture: | |
| Epoxy premix A | 2.5 g |
| ACH | 2.5 g |

The moulded shape was immersed in water at 28° C. and the release of ACH therefrom was monitored over a period of time and plotted (FIG. 7). As can be seen, the ACH is leached from the shape with essentially zero order release.

After leaching out the ACH, the residual matrix was fractured. An SEM was obtained and shows the pores are empty.

EXAMPLE 6

Repetition of Example 4 using a polyamide or a poly(meth) acrylamide in place of the styrene gives similar results.

EXAMPLE 7

A paste of the following composition was prepared:

| | |
|---|---|
| Hitad (acrylic resin) | 50 g |
| THF methacrylate | 5 g |
| $C_{12}$ methacrylate | 10 g |
| ACH | 50 g |
| Polyethylene oxide (PEO) | 5 g |
| Camphorquinone | 0.5 g |
| Dibutyl tin dilaurate | 0.5 g |

The paste was filled into a mould and cured with light of wavelength 247 nm for 15 minutes.

Figure 8:
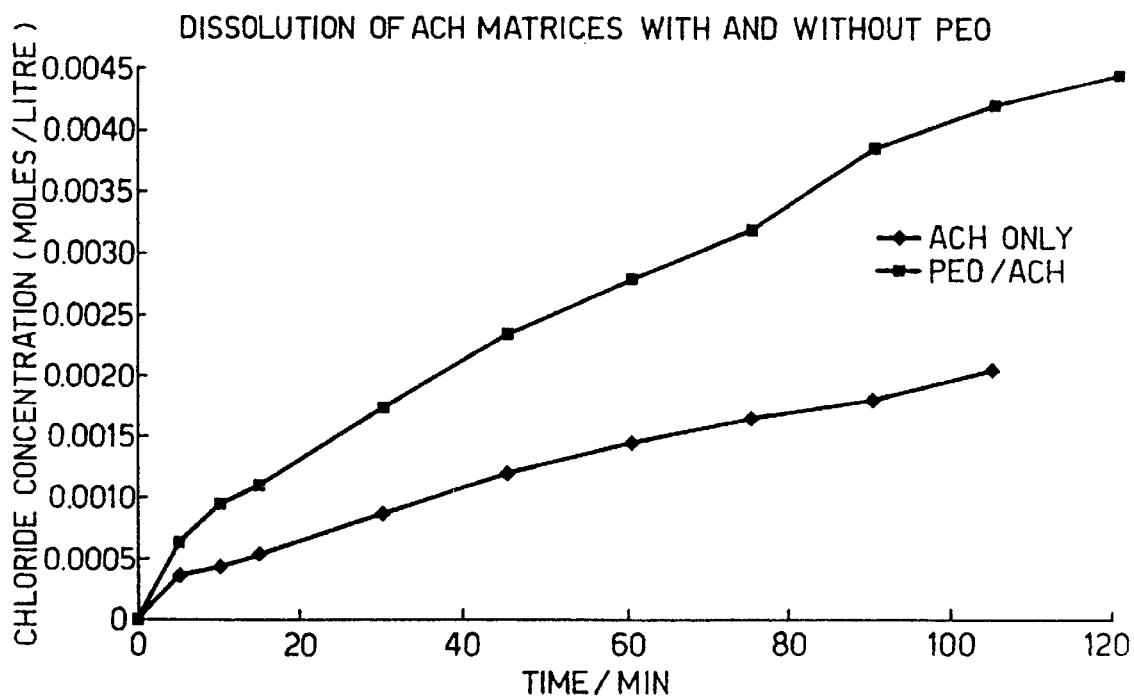

The hard cured shape was then immersed in water at 28° C. and the amounts of ACH and PEO leached therefrom were recorded against time. Both the ACH and the PEO were released linearly with time. FIG. 8 shows a plot of the release of the ACH (measured by chloride ion). FIG. 9 shows a plot of the release of PEO as measured by refractive index.

The experiment was repeated but without any PEO present in the paste. As can be seen from FIG. 8, the release rate for the ACH was enhanced by the incorporation of the PEO.

EXAMPLE 8

A paste of the following composition was prepared:

| | |
|---|---|
| Hitad (acrylic resin) | 50 g |
| THF methacrylate | 5 g |
| $C_{12}$ methacrylate | 10 g |
| ACH | 50 g |
| Cetyl pyridinium chloride (CPC) | 5 g |
| Camphorquinone | 0.5 g |
| Dibutyl tin dilaurate | 0.5 g |

The paste was placed in a mould and cured with light of wavelength 247 nm for 15 minutes.

Figure 10:
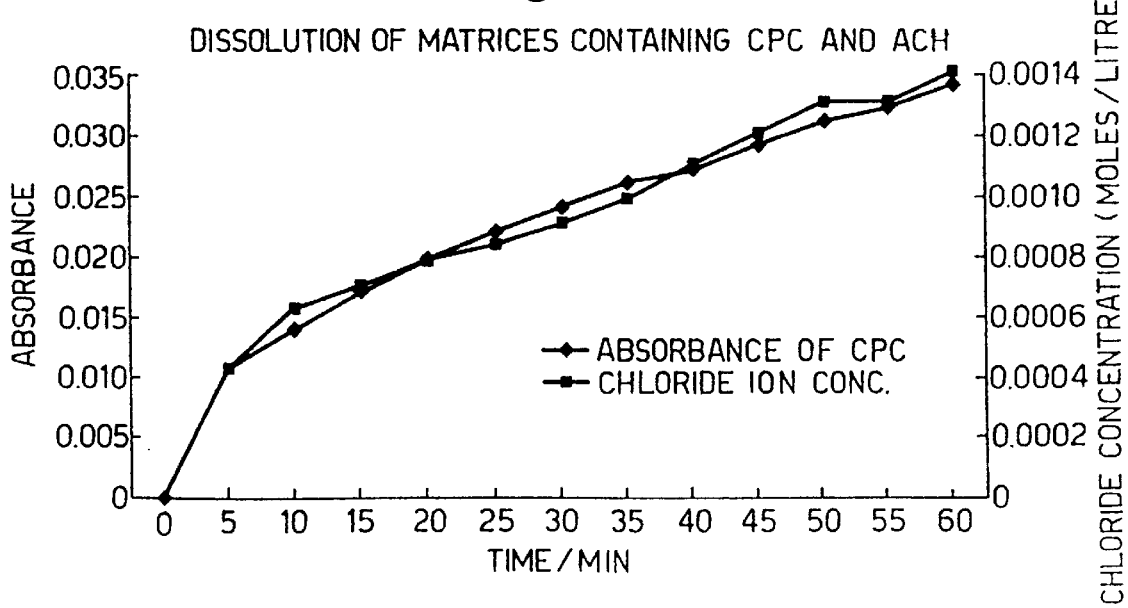

The hard solid shape removed from the mould was immersed in water at 28° C. and the release rates of the CPC and the chloride ion were monitored. Both were linear as is shown by FIG. 10. The chloride ion comes from both the ACH and the CPC. Using refractive index, we have also established that the release of ACH is linear.

EXAMPLE 9

The following mixture was prepared:

| | |
|---|---|
| Hitad (acrylic resin) | 50 g |
| PEG 1500 | 50 g |
| ACH | 50 g |
| THF methacrylate | 5 g |
| $C_{12}$ methacrylate | 10 g |
| Camphorquinone | 0.5 g |
| Dibutyl tin dilaurate | 0.5 g |

PEG 1500 is a liquid, and the above liquid mixture was cooled with stirring to 4° C. At this temperature, the PEG phase is separate from the resin, so that the PEG forms the interconnected pores. A portion of the mixture was light cured in a mould at 4° C.

The shaped block produced was immersed in water, and the ACH and PEG were released into the water. After leaching out the ACH and PEG, the block was examined by scanning electron microscope and was found to contain a continuous fine pore structure.

EXAMPLE 10

A cured block containing 38.5% ACH was made by the procedure of Example 2. The block was immersed in water for two weeks and then fractured. The internal structure was examined by scanning electron microscope which shows that the ACH has been extracted from the centre of the block.

EXAMPLE 11

A mixture of ACH and PEO in polyethylene was injection moulded to produce a shaped article of the invention. The release of ACH and PEO therefrom was linear. Similar results were obtained by injection moulding a mixture of ACH and PEO in PVC.

EXAMPLE 12

The following mixture was prepared:

| | |
|---|---|
| Hitad (acrylic resin) | 50 g |
| Polyethylene oxide (PEO) | 50 g |
| Menthol | 1 g |
| ACH | 50 g |
| THF methacrylate | 5 g |
| $C_{12}$ methacrylate | 10 g |

| | |
|---|---|
| Camphorquinone | 0.5 g |
| Dibutyl tin dilaurate | 0.5 g |

To keep the menthol and PEO in a phase separated from the resin, the mixture was cooled with stirring to 10° C. A portion of the mixture was light cured in a mould at 10° C.

The shaped block produced was rubbed on the skin and the release of menthol was evident.

Figure 2:
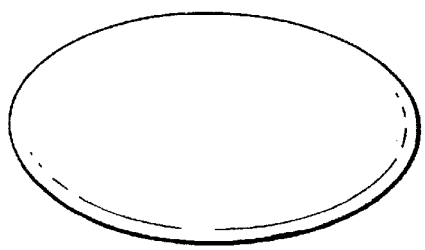
FIG. 2 is a side elevation of a first embodiment of article of the invention.
Figure 3:
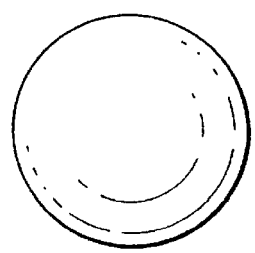
FIG. 3 is a front elevation of the article of FIG. 2.

Referring to FIGS. 2 and 3 of the drawings, the embodiment shown is ovoid in shape. It consists of a solid block of antiperspirant product of the invention, i.e. a water-insoluble matrix with antiperspirant distributed therein. These ovoid shapes can be made in any desired size, but will usually have a major dimension of about 3 or 4 inches and a minor dimension of about 2 inches.

Figure 4:
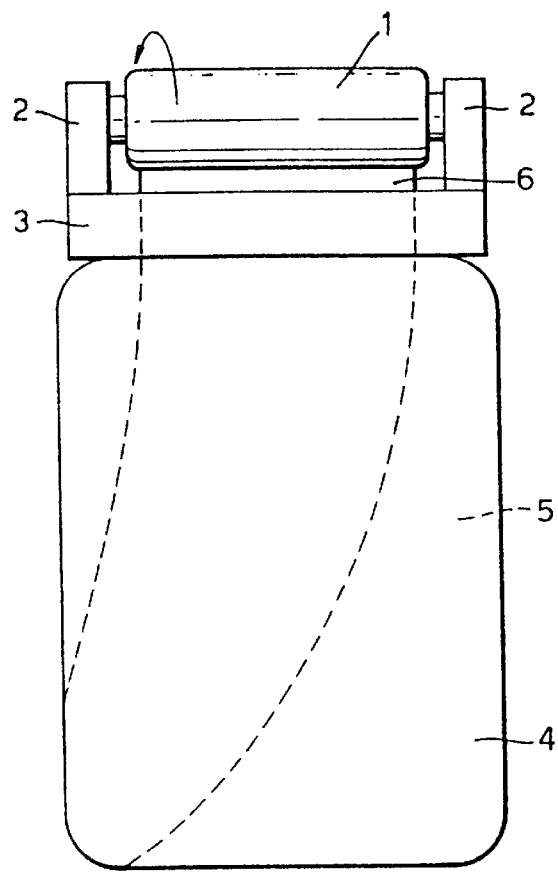
FIG. 4 is a schematic plan view of a second embodiment of article in association with a water reservoir.

In FIG. 4, the shaped article is in the form of a roller 1 rotatably mounted between arms 2 on support 3. The support is attached to a container 4, for example a bottle, which serves as a water (5) reservoir. A wick 6 extends from inside bottle 4, through an aperture in support 3, to contact the periphery of roller 1.

The roller 1 is made of an antiperspirant product of the invention and comprises a water-insoluble polymeric matrix having an antiperspirant distributed therein.

In use, the roller is moved over (and in contact with) an area of skin to which antiperspirant is to be applied. As the roller 1 rotates, it is wet by water from wick 6, and the water leaches antiperspirant from roller 1 and carries it onto the skin.

We claim:

1. An antiperspirant product which comprises a dry water-insoluble, porous, polymeric matrix having a solid, particulate antiperspirant homogeneously distributed therein in interconnecting pores thereof, the product being in the form of a hard shape having a porous structure which is substantially rigid and stable, wherein said polymeric matrix comprises a polyacrylate, polymethacrylate, epoxy, polystyrene, polyvinylchloride, phenol formaldehyde, polyurethane, polyolefin, polyamide, polyacrylamide, polymethacrylamide or silicone resin, whereby said product leaches said antiperspirant out of said matrix upon contact with water.

2. The antiperspirant product according to claim 1 wherein said polymeric matrix is cross-linked.

3. The antiperspirant product according to claim 1 wherein said polymeric matrix comprises polyacrylate or polymethacrylate and a plasticizer.

4. The antiperspirant product according to claim 3 wherein said plasticizer is selected from the group consisting of THF methacrylate and $C_{12}$ methacrylate.

5. The antiperspirant product according to claim 1 which additionally comprises an indicator which becomes visible upon depletion of the antiperspirant from said matrix.

6. The antiperspirant product according to claim 1 whereby said product leaches antiperspirant at a substantially constant rate.

7. The antiperspirant product according to claim 1 in the form of a shaped article.

8. The antiperspirant product according to claim 7 wherein said shaped article additionally includes a holder and a water reservoir adapted to wet said shaped article during use.

9. A method of applying antiperspirant to a surface which comprises wetting an antiperspirant product according to claim 1 and contacting said surface with said wet antiperspirant product.

10. A method of making an antiperspirant product which comprises forming a mixture of a solid particulate antiperspirant and matrix-forming monomer, polymerizing said matrix-forming monomer to form a dry water-insoluble, porous polymeric matrix with the antiperspirant homogeneously distributed therein in interconnecting pores thereof.

11. The method of claim 10 wherein said matrix-forming monomer includes an additive dissolved therein, which additive separates from said monomer upon cooling to form a discreet dispersed phase, thereby forming pores in said matrix upon polymerization.

* * * * *